United States Patent
Wisler et al.

[19]

[11] Patent Number: 6,163,151
[45] Date of Patent: Dec. 19, 2000

[54] APPARATUS AND METHOD FOR MAKING NUCLEAR MAGNETIC MEASUREMENTS IN A BOREHOLE

[75] Inventors: Macmillan M. Wisler, Kingwood; David M. Schneider, Spring, both of Tex.

[73] Assignee: Baker Hughes Incorporated, Houston, Tex.

[21] Appl. No.: 09/150,137

[22] Filed: Sep. 9, 1998

[51] Int. Cl.[7] .................................................. G01V 3/00
[52] U.S. Cl. .................................... 324/303; 324/306
[58] Field of Search ................................ 324/303, 318, 324/322, 306

[56] References Cited

U.S. PATENT DOCUMENTS

| | | | |
|---|---|---|---|
| 3,597,681 | 8/1971 | Huckebay et al. | 324/0.5 R |
| 3,617,867 | 11/1971 | Herzog . | |
| 4,350,955 | 9/1982 | Jackson et al. | 324/303 |
| 4,710,713 | 12/1987 | Strikman | 324/303 |
| 4,714,881 | 12/1987 | Givens | 324/303 |
| 4,717,876 | 1/1988 | Masi et al. | 324/303 |
| 4,717,877 | 1/1988 | Taicher et al. | 324/303 |
| 5,280,243 | 1/1994 | Miller | 324/303 |
| 5,376,884 | 12/1994 | Sezginer | 324/303 |
| 5,486,761 | 1/1996 | Sezginer | 324/303 |
| 5,572,132 | 11/1996 | Pulyer et al. . | |
| 5,629,623 | 5/1997 | Sezginer | 324/303 |
| 5,705,927 | 1/1998 | Sezginer et al. . | |

FOREIGN PATENT DOCUMENTS

| | | |
|---|---|---|
| 0 618 458 A2 | 10/1994 | European Pat. Off. . |
| 2 324 375 | 10/1998 | United Kingdom . |
| 2 325 981 | 12/1998 | United Kingdom . |

*Primary Examiner*—Christine K. Oda
*Assistant Examiner*—Brij B. Shrivastav
*Attorney, Agent, or Firm*—Madan, Mossman & Sriram P.C.

[57] ABSTRACT

An NMR logging tool has a conducting permanent magnet with its axis parallel to the borehole axis to produce a static field in a portion of the formation surrounding a borehole that is parallel to the borehole axis. A dipole RF antenna with the dipole axis orthogonal to the borehole axis is used to produce an RF magnetic field orthogonal to the static field. The same antenna is used to receive the echo signals from excited nuclei in the formation. A number of gapped ferrite strips on the permanent magnet shield the permanent magnet from the RF field and enhance the RF field. Another form of the tool may be used for making Measurement-While-Drilling measurements with the permanent magnet set in a recess on a drilling collar.

21 Claims, 5 Drawing Sheets

APPARATUS AND METHOD FOR MAKING NUCLEAR MAGNETIC MEASUREMENTS IN A BOREHOLE

BACKGROUND OF THE INVENTION

1. Field of the Invention

This invention relates to borehole measurements and more particularly to borehole measurements employing nuclear magnetic resonance.

2. Background of the Art

There are known in the patent literature various techniques for carrying out borehole measurements employing Nuclear Magnetic Resonance (NMR). In most such devices, a static magnetic field is used to align the magnetic spin of nucleii in the formation to in a preferential direction. Earlier devices used the earth's magnetic field as the static field while in recent years, static fields of greater strength have been produced by means of permanent magnets. A Radio Frequency (RF) transmitter is used to produce a magnetic field in the formation with its field direction orthogonal to the static magnetic field: this RF field causes a precession of the spins of the nucleii. Electromagnetic signals produced by this precession are detected by a receiver and analyzed to give information about the formation. The characteristics of this precession signal are related to the strength of the static magnetic field, the type of the nucleii and the frequency of the RF signal. One of the desirable characteristics of an NMR measuring device is to be able to produce a strong static field that is relatively uniform in the direction of tool travel over a substantial portion of the formation (to increase the signal-to-noise ratio and to reduce the effect of tool motion) and away from the borehole (to avoid signals from borehole fluids).

U.S. Pat. No. 4,350,955 discloses a device in which the static magnetic field is produced by a pair of permanent magnets with like poles opposing each other across a gap. The magnets have their magnetization axis along the longitudinal axis of the tool and borehole. The region of examination produced by this device is a toroid centered on the longitudinal axis and the gap between the permanent magnets. The static magnetic field within the region of examination is radial with respect to the longitudinal axis of the tool. The RF field is produced by a coil antenna with its axis parallel to the longitudinal axis and has a direction parallel to the longitudinal axis, producing the necessary orthogonality to the static field. This particular device suffers from a number of drawbacks. The region of examination is quite limited in the axial direction, so that the echo signals from the precession are weak. The device is susceptible to errors because of the motion of the tool. In addition, the static field also has a region within the borehole where the magnitude may be substantially the same as in the toroidal region, giving rise to a fairly strong echo signal from borehole fluids.

U.S. Pat. Nos. 5,212,447 and 5,280,243 disclose devices in which the region of examination is cylindrical. The static magnetic field is produced by cylindrical magnets with a magnetic axis perpendicular to the axis of the cylinder and the borehole. With a sufficiently long cylindrical magnet, the static field is approximately that of a line dipole and has a cylindrical region centered on the longitudinal axis in which the field is substantially constant. The direction of the static field may be radial, circumferential, or in between, depending upon the azimuthal position with respect to the magnet axis. The RF field is produced by a rectangular loop antenna with the plane of the rectangle parallel to the longitudinal axis of the borehole. This loop antenna effectively acts as a dipole that is orthogonal to the line dipole of the static field, so that the RF field within a large portion of the cylindrical region of examination is orthogonal to the static field. However, there will be portions where the two fields are not exactly orthogonal, effectively diminishing the size of the region of examination where orthogonality exists.

The essential difference between the devices of U.S. Pat. Nos. 5,212,447 and 5,280,243 is that the former is designed for wireline applications while the latter is designed for MWD applications. In both devices, by making the magnets longer, the region of examination can be extended, thus increasing the magnitude of the echo signal. The former device also has a gradient coil for reducing the effect of echo signals from the borehole fluids.

In both devices, the permanent magnet has to be made of a non-conducting material. This is necessary because the RF coil surrounds the permanent magnet and if the magnet were made conducting, induced currents in the magnet would reduce the efficiency of the tool. In addition, the presence of a conducting core inside the RF antenna severely distorts the RF magnetic field. Non-conducting permanent magnets are inherently not as powerful as conducting permanent magnets made of Samarium-Cobalt or of Neodymium-Iron. Consequently, to produce a given static magnetic field strength in the region of examination, devices using non-conducting magnets require a larger magnet size than comparable devices in which a conducting magnet may be used. In addition, the induced currents would also be detrimental to the efficiency of the RF antenna.

Furthermore, due to the fact that the static and magnetic fields are produced by line dipoles mechanically oriented along the axis of the tool (but with orthogonal magnetic orientation), known field enhancement techniques such as using ferrite cores or yokes cannot be used with the RF antenna of prior art devices: such a ferrite device would effectively short the static field. If ferrite yokes could be used as part of the RF antenna design, the antennas themselves could be made more compact to attain a given field strength and a given signal-to-noise ratio in operation.

There is a need for an NMR tool that takes advantage of the inherently higher magnetic fields attainable by the use of conducting permanent magnets. Such a device should also be able to obtain improved signal-to-noise ratio for the RF antenna. The present invention satisfies this need.

SUMMARY OF THE INVENTION

The present invention is a device for obtaining NMR measurements using a tool deployed inside a borehole. One embodiment of the invention is suitable for use on a wireline while a second embodiment is suitable for use in a Measurement-While-Drilling (MWD) environment. A cylindrical magnet is used to produce a static magnetic field in the formation surrounding the borehole such that the field direction is parallel to the axis of the borehole within a region of examination. An RF antenna that effectively operates as a line dipole transmits an RF signal that produces an RF magnetic field in the region of examination that is orthogonal to the static field in the region of examination. This RF field may be radial or circumferential with respect to the axis of the borehole, depending upon the azimuth with respect to the dipole magnetic axis. The same or similarly oriented antenna is used as a receiver to detect the echo signals from excited nucleii in the region of examination.

The device may provided with a number of ferrite strips to focus the RF magnetic field. The spacing between the ferrite strips is sufficiently large to ensure that the static magnetic field is not adversely affected, but close enough to provide an RF field of sufficient uniformity in the axial direction.

BRIEF DESCRIPTION OF THE DRAWINGS

For a detailed understanding of the present invention, reference should be made to the following detailed description of the preferred embodiment, taken in conjunction with the accompanying drawings, in which like elements have been given like numerals, wherein.

DETAILED DESCRIPTION OF PREFERRED EMBODIMENTS

The various concepts of the present invention will be described in reference to FIGS. 1–4, which show schematic illustrations of embodiments of the device of the present invention.

Figure 1:
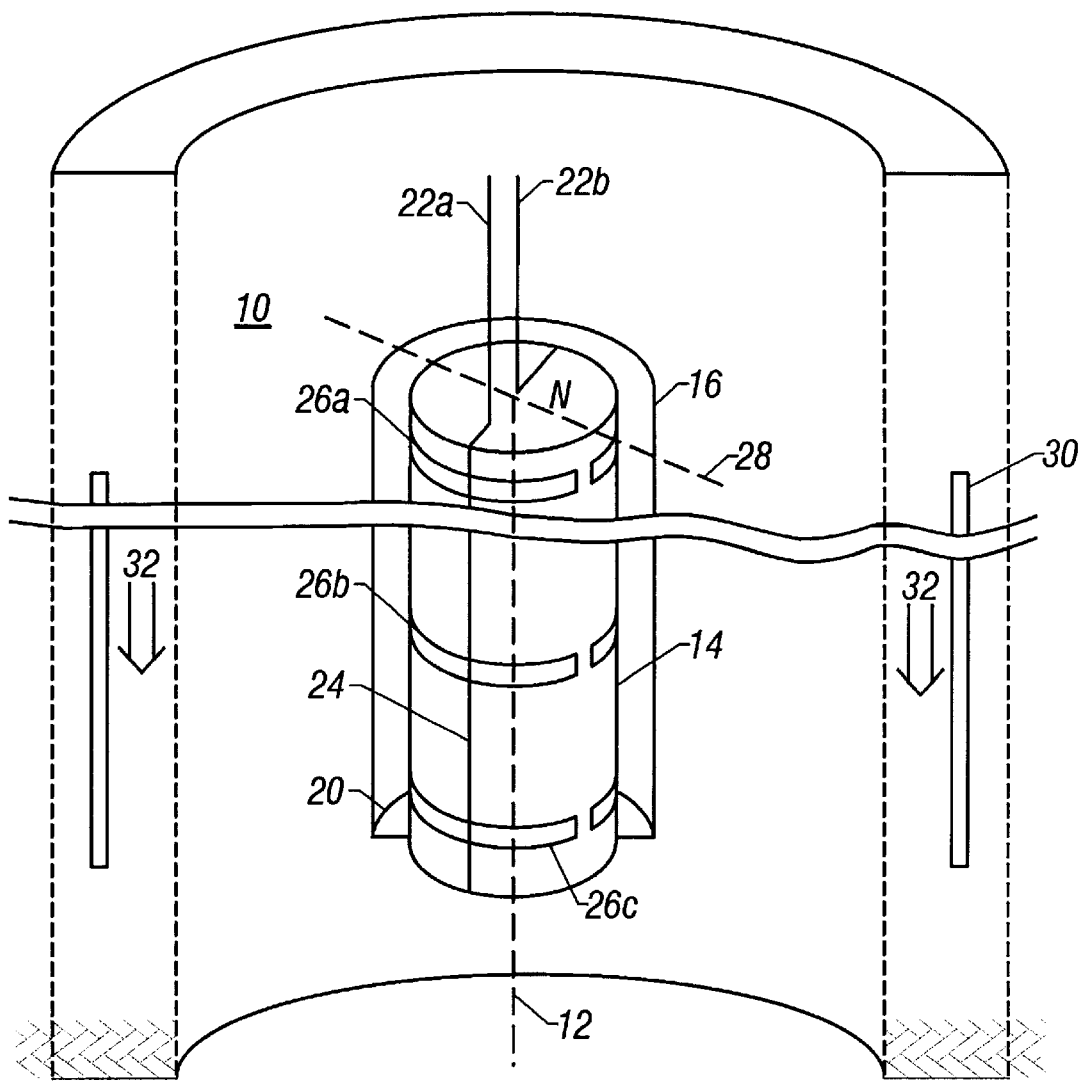
FIG. 1 is a schematic illustration of an apparatus suitable for deploying on a wireline for making NMR measurements inside a borehole in accordance with an embodiment of the present invention.

FIG. 1 shows a borehole 10 inside which a tool 20 according to a preferred embodiment of the present invention is deployed. The tool is deployed on a wireline (not shown). The borehole has a longitudinal axis 12. The axis of the tool 20 substantially coincides with the longitudinal axis 12 of the borehole 10. The tool includes a non-conducting, non-magnetic housing 16. Inside the housing is a cylindrical permanent magnet 14 having both its longitudinal axis and its magnetic axis substantially coinciding with the longitudinal axis 12 of the borehole, i.e., the north pole and the south pole of the magnet are on opposite sides of the flat ends of the cylinder 14. For illustrative purposes only, the magnet 14 is shown with its north pole on the upper surface of the cylinder.

An RF antenna having one or more windings 24 wrapped around the permanent magnet 14. Suitable antenna leads 22a, 22b connect the antenna to the electronic circuitry (not shown) for transmitting and receiving signals and for processing the received signals. Such electronic circuitry would be known to those versed in the art and is not discussed further.

The windings 24 define a substantially rectangular antenna wherein the plane of the antenna includes the longitudinal axis of the borehole and the permanent magnet axis. The longitudinal dimension of the antenna is preferably much longer than its width. Those versed in the art would recognize that this antenna, when pulsed with an RF electric current, will produce a magnetic field along the direction 28 that is perpendicular to the axis 12 of the permanent magnet. The field pattern is that of a line dipole and has a constant amplitude in the cylindrical region 30. Deployed around the permanent magnet 14 are a plurality of ferrite strips 26a, 26b, 26c. These ferrite strips go around the permanent magnet but are gapped in the directions corresponding to the RF dipole axis 28. The function of these ferrite strips is discussed below.

The permanent magnet 14 produces a static field in the formation indicated by the arrows 32. Within a cylindrical region 30 in the formation, the strength of the static field is substantially constant. This region 30 is the region of examination. The RF field produced by the antenna, as in the devices of U.S. Pat. Nos. 5,212,447 and 5,280,243 lies almost entirely in a plane orthogonal to the axis of the borehole. However, unlike in the prior art devices, the RF field is orthogonal to the static field over the entire cylindrical region of examination, rather than in just portions of the cylindrical region.

The ferrite strips serve two functions. First, the strips conduct the RF field around the permanent magnet: this makes it possible to use electrically conducting permanent magnets. As noted above, permanent magnets made of electrically conducting material can produce much higher field strengths than is possible with the use of non-conducting materials. Secondly, the ferrite strips also focus the RF magnetic field along the magnetic dipole axis.

Such ferrite strips could not have been used in the prior art devices of U.S. Pat. Nos. 5,212,447 and 5,280,243. In those prior art devices, the magnetic poles of the permanent magnets are located on the curved surfaces of the magnets, so that ferrite strips as shown in FIG. 1 would offer a very low reluctance to the static magnetic field and would effectively "short" the static magnetic field. In the present invention, the magnetic poles of the permanent magnets are located on the flat ends of the cylinder 14, so that the same configuration of ferrite strips has a much higher reluctance in the magnetic circuit of the static field.

The number of ferrite strips that are used is a tradeoff between two conflicting requirements. On the one hand, it is desirable to have as many strips as possible, so as to increase the shielding of the permanent magnet and reduce a ripple effect on the RF magnetic field. On the other hand, it is desirable to reduce the number of strips in order to keep the perturbation of the static magnetic field as small as possible. Determination of the number of strips to be used can be based upon prior art methods of calculating the aforesaid effects.

Figures 2A, 2B:
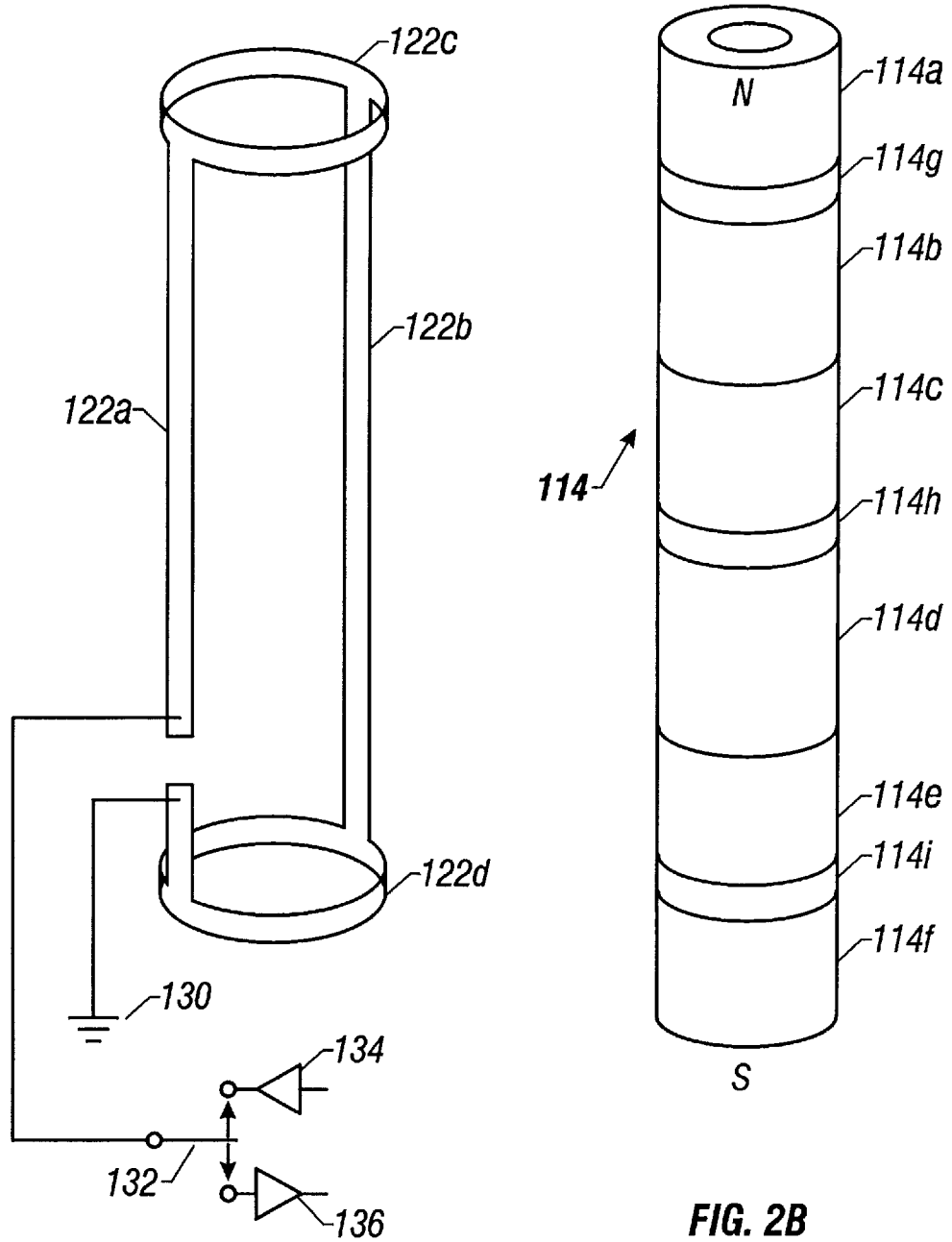
FIGS. 2A, 2B schematically alternate arrangements of the RF coil and the permanent magnets

FIG. 2A is a schematic illustration of an alternate arrangement of the RF antenna loop. Two longitudinal conductors 122a, 122b are connected at their ends by ring conductors 122c, 122d. One lead from the conductors is grounded 130 and the other lead goes to a switch 132 that switches the coil from a transmit position, indicated by connection to the transmitter 134, to the receive position, indicated by connection to the receiver 136. The transmitter 134 and receiver 136 are deployed on the housing of the tool and are not discussed further as they are known in prior art.

FIG. 2B illustrates that the permanent magnet 114 in the device could consist of a number of segments 114a–114i without detracting from the invention. This is for focusing of the static field and for ease of construction and reduced cost, since large permanent magnets arc difficult and expensive to construct. The segments can be a combination of permanent magnets, denoted for illustrative purposes by the six magnets 114a–114f, and combinations of materials with high magnetic permeability (such as iron) and low permeability segments (such as non-magnetic steel) 114g–114i. These can be stacked in such a way as to adjust the permanent magnetic field in the region 30 to have a substantially axial direction and to have a substantially uniform magnitude at all azimuths. The ferrite strips 26 of FIG. 1 are not shown in FIG. 2B to simplify the illustration.

Figure 3:
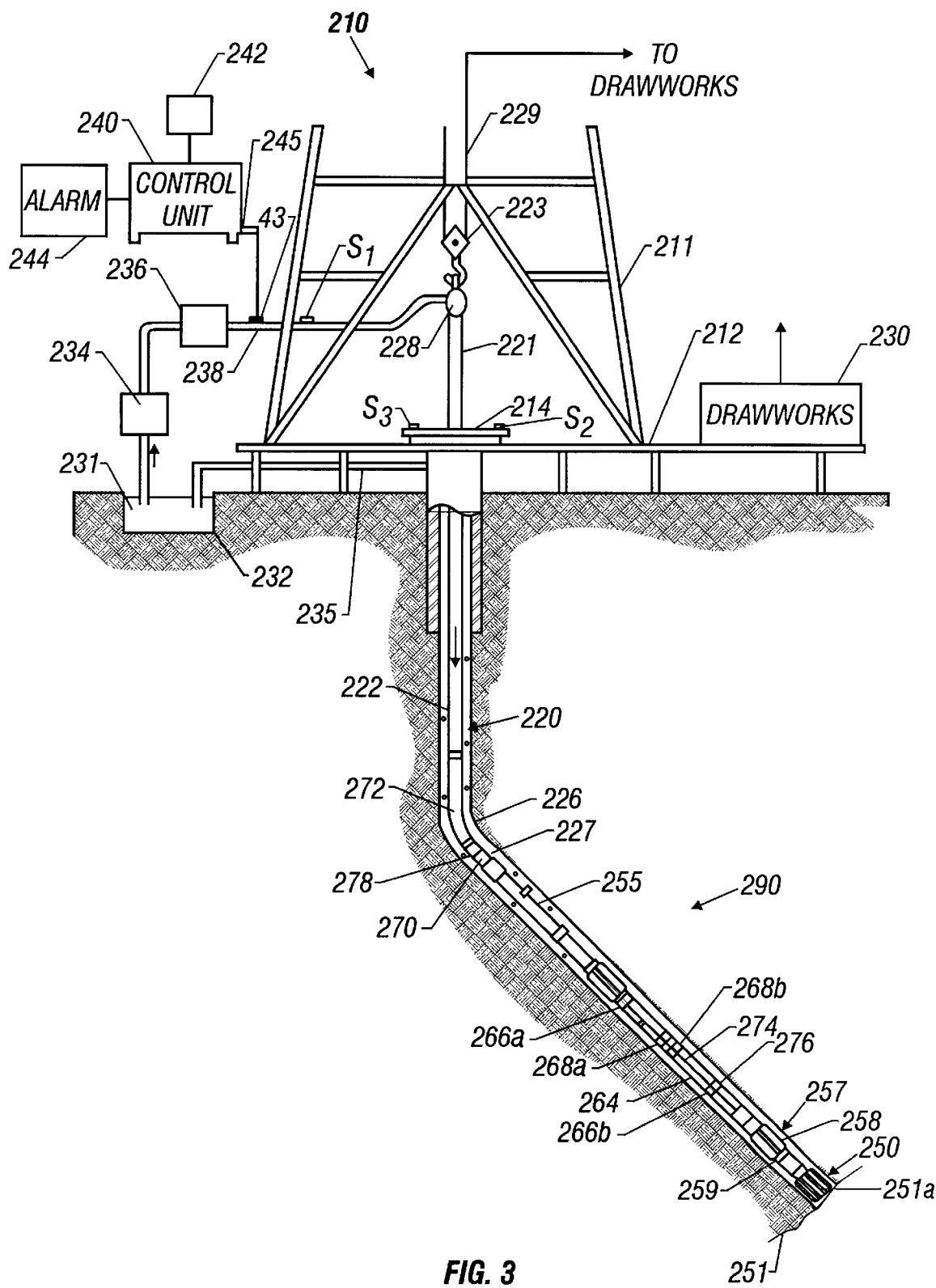
FIG. 3 is a schematic illustration of a drilling assembly incorporating a Measurement-While-Drilling embodiment of the present invention.

An embodiment of the present invention may also be used for making Measurements-While-Drilling. FIG. 3 shows a schematic diagram of a drilling system 210 having a drilling assembly 290 shown conveyed in a borehole 226 for drilling the wellbore. The drilling system 210 includes a conventional derrick 211 erected on a floor 212 which supports a rotary table 214 that is rotated by a prime mover such as an electric motor (not shown) at a desired rotational speed. The drill string 220 includes a drill pipe 222 extending downward from the rotary table 214 into the borehole 226. The drill bit 250 attached to the end of the drill string breaks up the geological formations when it is rotated to drill the borehole 226. The drill string 220 is coupled to a drawworks 230 via a Kelly joint 221, swivel, 228 and line 229 through a pulley 223. During drilling operations, the drawworks 230 is operated to control the weight on bit, which is an important parameter that affects the rate of penetration. The operation of the drawworks is well known in the art and is thus not described in detail herein.

During drilling operations, a suitable drilling fluid 231 from a mud pit (source) 232 is circulated under pressure through the drill string by a mud pump 234. The drilling fluid passes from the mud pump 234 into the drill string 220 via a desurger 236, fluid line 228 and Kelly joint 221. The drilling fluid 231 is discharged at the borehole bottom 251 through an opening in the drill bit 250. The drilling fluid 231 circulates uphole through the annular space 227 between the drill string 220 and the borehole 226 and returns to the mud pit 232 via a return line 235. A sensor $S_1$ preferably placed in the line 238 provides information about the fluid flow rate. A surface torque sensor $S_2$ and a sensor $S_3$ associated with the drill string 220 respectively provide information about the torque and rotational speed of the drill string. Additionally, a sensor (not shown) associated with line 229 is used to provide the hook load of the drill string 220.

In one embodiment of the invention, the drill bit 250 is rotated by only rotating the drill pipe 222. In another embodiment of the invention, a downhole motor 255 (mud motor) is disposed in the drilling assembly 290 to rotate the drill bit 250 and the drill pipe 222 is rotated usually to supplement the rotational power, if required, and to effect changes in the drilling direction.

In one preferred embodiment of FIG. 3, the mud motor 255 is coupled to the drill bit 250 via a drive shaft (not shown) disposed in a bearing assembly 257. The mud motor rotates the drill bit 250 when the drilling fluid 231 passes through the mud motor 255 under pressure. The bearing assembly 257 supports the radial and axial forces of the drill bit. A stabilizer 258 coupled to the bearing assembly 257 acts as a centralizer for the lowermost portion of the mud motor assembly.

In one embodiment of the invention, a drilling sensor module 259 is placed near the drill bit 250. The drilling sensor module contains sensors, circuitry and processing software and algorithms relating to the dynamic drilling parameters. Such parameters preferably include bit bounce, stick-slip of the drilling assembly, backward rotation, torque, shocks, borehole and annulus pressure, acceleration measurements and other measurements of the drill bit condition. The drilling sensor module processes the sensor information and transmits it to the surface control unit 240 via a suitable telemetry system 272.

Figure 4:
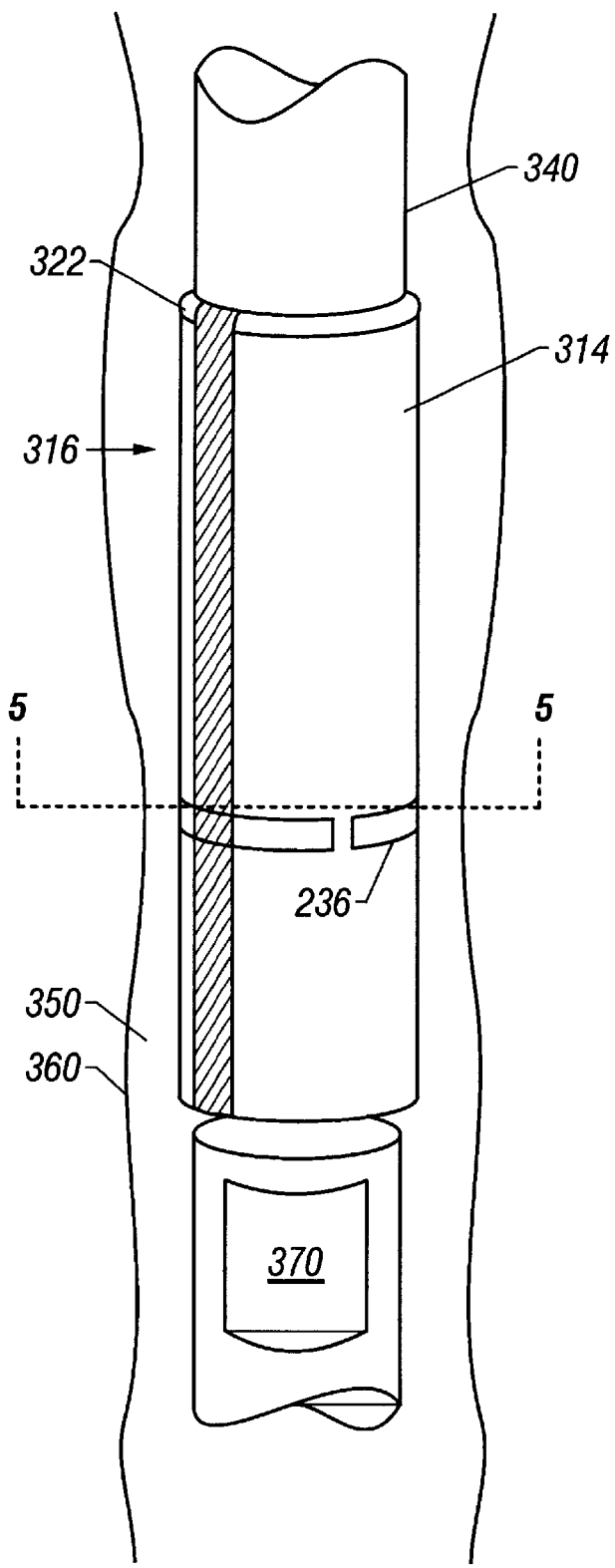
FIG. 4 is an perspective illustration of the invention as adapted for making Measurement-While-Drilling.
Figure 5:
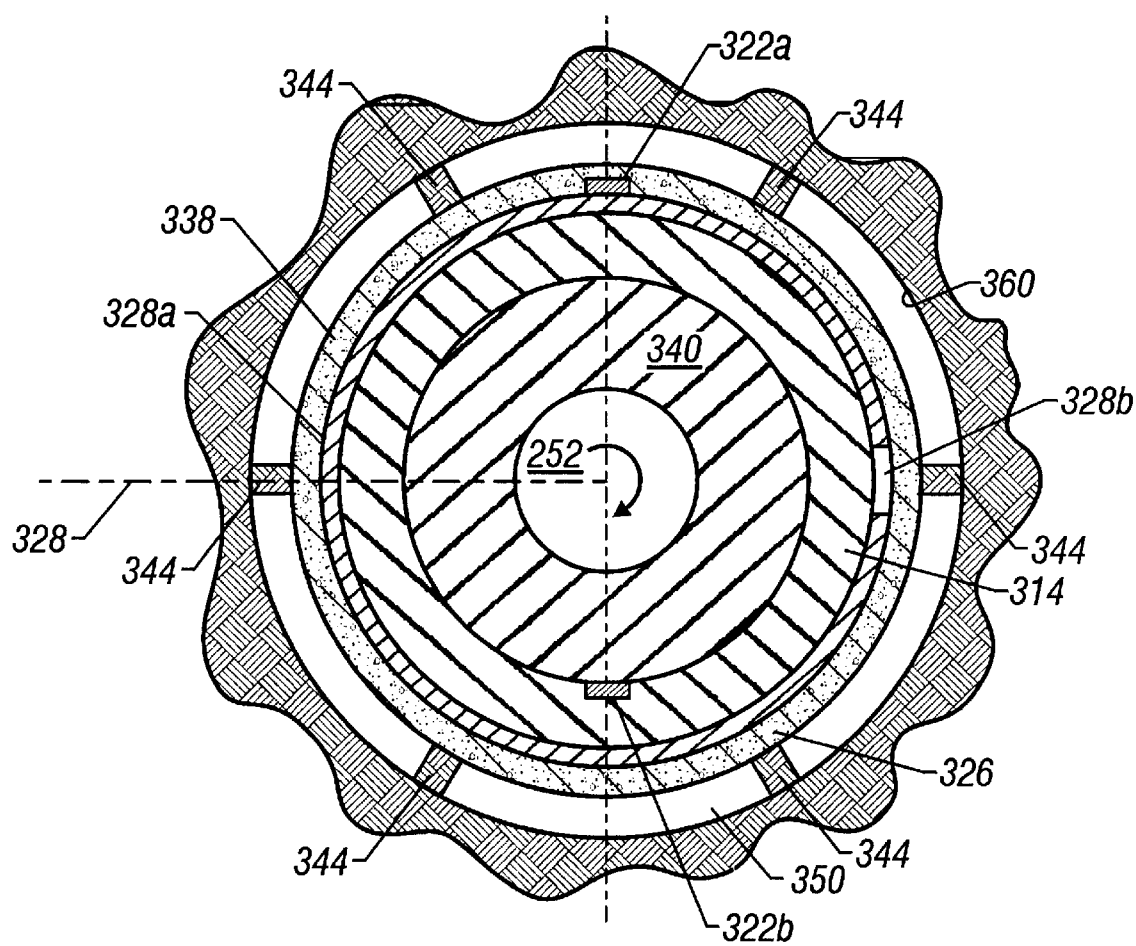
FIG. 5 is a sectional view of the device of FIG. 4.

A special segment of drill pipe 270, discussed in more detail in FIGS. 4–5 incorporates some of the novel aspects of the present invention. In FIG. 3, this is shown as being above the mud motor 58. The invention discussed below with reference to FIGS. 4–5 could also be located between the mud motor and the drill bit 51. Alternatively, the mud motor 58 and the associated equipment may be absent and the drill bit 51 may be rotated by the drill pipe.

FIG. 4 is a perspective illustration of the present invention as adapted for making Measurements-While-Drilling while FIG. 5 shows the MWD device in sectional view. The device 316 is shown inside a borehole 350 with walls 360. The device is supported on a drilling collar 340, with the permanent magnet 314 and the RF antenna 322 set in a recess in the drilling collar. The electronic circuitry 370 is located in a suitable cavity in the drilling collar.

Referring to FIG. 5, a "necked down" section of the drilling collar 340 has a bore 352 therethrough for carrying drilling fluid. The permanent magnet 314 in the MWD device is in the shape of a ring surrounding the drilling collar 340. The ferrite strip 326 surrounds most of the permanent magnet 314 except for gaps 328a, 328b. The RF antenna 322a, 322b is positioned orthogonal to the gaps 328a, 328b so that the RF field is focused along the RF antenna dipole axis 328. The entire device is maintained in a central position in the borehole by means of stabilizers 344. A suitable protective coating 338 shields the permanent magnet and the antenna from the action of drilling fluid.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A well logging apparatus for determining a parameter of interest of a formation having a borehole with a longitudinal axis therein, said apparatus comprising:
   (a) a permanent magnet arrangement having a magnetic axis substantially parallel to said longitudinal axis, said permanent magnet arrangement generating a static magnetic field in a region of examination of a portion of the formation adjacent the logging apparatus, said static magnetic field being substantially parallel to the longitudinal axis in the region of examination; and
   (b) at least one radio frequency (RF) antenna acting substantially like a line dipole exterior to the permanent magnet arrangement, said at least one RF antenna adapted to
      (i) produce an RF magnetic field that is substantially orthogonal to said static magnetic field in said region of examination,
      (ii) excite nuclei in said region of examination, and
      (iii) receive nuclear magnetic resonance signals from the excited nuclei and to provide an output signal indicative of the parameter of interest.

2. The well logging apparatus of claim 1 wherein the region of examination is substantially cylindrical and centered on the longitudinal axis.

3. The well logging apparatus of claim 1 further comprising a plurality of ferrite strips encircling the permanent magnet arrangement for focusing said RF field.

4. The well logging apparatus of claim 1 wherein the permanent magnet comprises electrically conductive components.

5. The well logging apparatus of claim 4 wherein the permanent magnet arrangement is made from a material selected from the group consisting of: (i) samarium-cobalt, and (ii) neodymium-iron.

6. The well logging apparatus of claim 1 wherein the permanent magnet arrangement further comprises a plurality of permanent magnets arranged end-to-end.

7. The well logging apparatus of claim 6, permanent magnet arrangement further comprising a plurality of elements made of at least one of (i) a magnetic conductor, and (ii) a non-magnetic materials, said elements being arranged to obtain a substantially constant magnetic field strength in the region of examination.

8. A Measurement-While-Drilling (MWD) apparatus for obtaining measurements of a parameter of interest of a formation having a borehole with a longitudinal axis therein, said apparatus comprising:

(a) a drilling collar for carrying a drill-bit for drilling the borehole;

(b) a permanent magnet arrangement set in a recess on the drilling collar for generating a static magnetic field in a region of examination of a portion of the formation adjacent the MWD apparatus, said permanent magnet arrangement having a magnetic axis substantially parallel to said longitudinal axis, said static magnetic field being substantially parallel to the longitudinal axis in the region of examination; and (c) a radio frequency (RF) antenna acting substantially like a line dipole exterior to the permanent magnet arrangement, said RF antenna adapted to:
  (i) produce an RF magnetic field that is substantially orthogonal to said static magnetic field in said region of examination,
  (ii) excite nuclei in said region of examination, and
  (iii) receive nuclear magnetic resonance signals from the excited nuclei and to provide an output signal indicative of the parameter of interest.

9. The MWD apparatus of claim 8 wherein the region of examination is substantially cylindrical and centered on the longitudinal axis.

10. The MWD apparatus of claim 8 further comprising a plurality of gapped ferrite strips encircling the permanent magnet arrangement for focusing said RF field.

11. The MWD apparatus of claim 8 wherein the permanent magnet arrangement comprises electrically conductive components.

12. The MWD apparatus of claim 11 wherein the permanent magnet arrangement is made from a material selected from the group consisting of: (i) samarium-cobalt, and (ii) neodymium-iron.

13. The MWD apparatus of claim 8 wherein the permanent magnet arrangement further comprises a plurality of permanent magnets arranged end-to-end.

14. The MWD apparatus of claim 13, the permanent magnet arrangement further comprising plurality of elements made of at least one of (i) a magnetic conductor, and (ii) a non-magnetic materials, said elements being arranged to obtain a substantially constant magnetic field strength in the region of examination.

15. A method of obtaining measurements of a parameter of interest of a formation having a borehole with a longitudinal axis therein, said method comprising:

(a) using a tool having a permanent magnet arrangement with a magnetic axis substantially parallel to said longitudinal axis to generate a static magnetic field in a region of examination of a portion of the formation adjacent the tool, said static magnetic field being substantially parallel to the longitudinal axis in the region of examination; and (b) using at least one radio frequency (RF) antenna acting substantially like a line dipole on the tool for:
  (i) generating a radio frequency magnetic field substantially orthogonal to said static magnetic field in said region of examination to excite nucleii therein, and
  (ii) receiving signals from said excited nucleii indicative of the parameter of interest.

16. The method of claim 15, further comprising using a plurality of ferrite strips encircling the permanent magnet arrangement for focusing said RF field.

17. The method of claim 15 further comprising using a plurality of elements made of at least one of (i) a magnetic conductor, and (ii) a non-magnetic materials, for obtaining a substantially constant magnetic field strength in the region of examination.

18. A method of obtaining measurements of a parameter of interest of a formation while drilling a borehole with a longitudinal axis therein, said method comprising:

(a) using a permanent magnet arrangement set in a recess of a drilling collar to generate a static magnetic field in a region of examination of a portion of the formation adjacent the borehole, said static magnetic field being substantially longitudinal in the region of examination;

(b) using at least one radio frequency (RF) antenna acting substantially like a line dipole on the exterior of the permanent magnet arrangement to:
  (i) generate a radio frequency magnetic field substantially orthogonal to said static magnetic field in said region of examination to excite nucleii therein, and
  (ii) receive signals from said excited nucleii indicative of the parameter of interest; and (c) continuing drilling operations with a drill bit conveyed on the drilling collar.

19. The method of claim 18, further comprising using a plurality of ferrite strips encircling the permanent magnet arrangement for focusing said RF field.

20. The method of claim 18 further comprising using a plurality of elements made of at least one of (i) a magnetic conductor, and (ii) a non-magnetic materials, for obtaining a substantially constant magnetic field strength in the region of examination.

21. A well logging apparatus for determining a parameter of interest of a formation having a borehole with a longitudinal axis therein, said apparatus comprising:

(a) a permanent magnet arrangement having a magnetic axis substantially parallel to said longitudinal axis, said permanent magnet arrangement generating a static magnetic field in a region of examination of a portion of the formation adjacent the logging apparatus, said static magnetic field being substantially parallel to the longitudinal axis in the region of examination;

(b) at least one radio frequency (RF) antenna acting substantially like a line dipole exterior to the permanent magnet arrangement, said at least one RF antenna adapted to
  (i) produce an RF magnetic field that is substantially orthogonal to said static magnetic field in said region of examination,
  (ii) excite nuclei in said region of examination, and
  (iii) receive nuclear magnetic resonance signals from the excited nuclei and to provide an output signal indicative of the parameter of interest; and (c) a plurality of ferrite strips encircling the permanent magnet arrangement for focusing said RF field.

* * * * *